United States Patent
Bruder et al.

(10) Patent No.: US 7,818,046 B2
(45) Date of Patent: Oct. 19, 2010

(54) MEDICAL IMAGING METHOD AND AN ASSOCIATED APPARATUS

(75) Inventors: Herbert Bruder, Höchstadt (DE); Rainer Raupach, Adelsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 470 days.

(21) Appl. No.: 11/498,798

(22) Filed: Aug. 4, 2006

(65) Prior Publication Data
US 2007/0032735 A1 Feb. 8, 2007

(30) Foreign Application Priority Data
Aug. 5, 2005 (DE) .................... 10 2005 036 963

(51) Int. Cl.
*A61B 5/05* (2006.01)
(52) U.S. Cl. .................. 600/428; 600/410; 600/407; 600/425; 378/8
(58) Field of Classification Search .......... 600/407, 600/410, 425, 428; 378/8
See application file for complete search history.

(56) References Cited
U.S. PATENT DOCUMENTS
7,145,982 B2 * 12/2006 Ikeda et al. .................... 378/16

2004/0077941 A1 * 4/2004 Reddy et al. ............... 600/428
2005/0089133 A1 * 4/2005 Tsuyuki ....................... 378/8
2005/0090737 A1 * 4/2005 Burrell et al. .............. 600/428

FOREIGN PATENT DOCUMENTS
JP  2000051208 A  2/2000
WO  WO 2004006771 A1  1/2004

OTHER PUBLICATIONS
Chinese Office Action for Chinese Application No. 2006101107270 (English translation).
Japanese Office Action dated Apr. 27, 2010 for Japanese Application no. 2006-212827 (English Translation).

* cited by examiner

*Primary Examiner*—Long V Le
*Assistant Examiner*—Nigel Fontenot
(74) *Attorney, Agent, or Firm*—Harness, Dickey & Pierce, P.L.C.

(57) ABSTRACT

In the course of an imaging method that is particularly suitable for creating an image data record of the heart and/or the blood vessels of a patient, a series of recording pulses, tuned to the cardiac rhythm, are derived from an ECG signal of the cardiac rhythm of the patient. The imaging is driven in a pulsed fashion from the series of recording pulses. In this case, an initial instant and a final instant of a future recording pulse are determined by taking account of at least one variability parameter characterizing the irregularity of the cardiac rhythm.

14 Claims, 3 Drawing Sheets

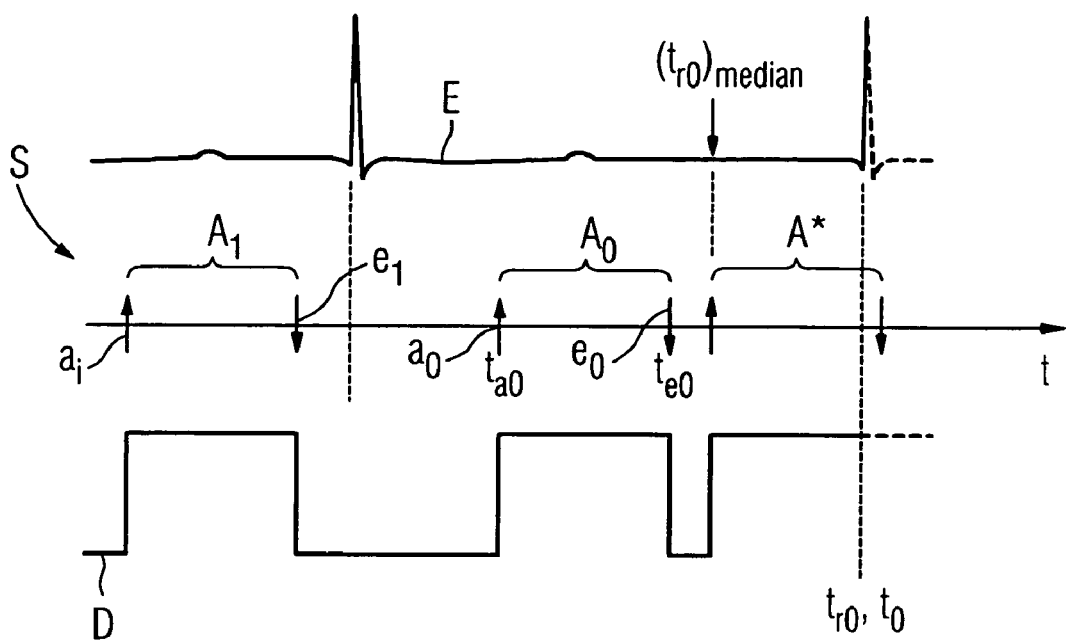
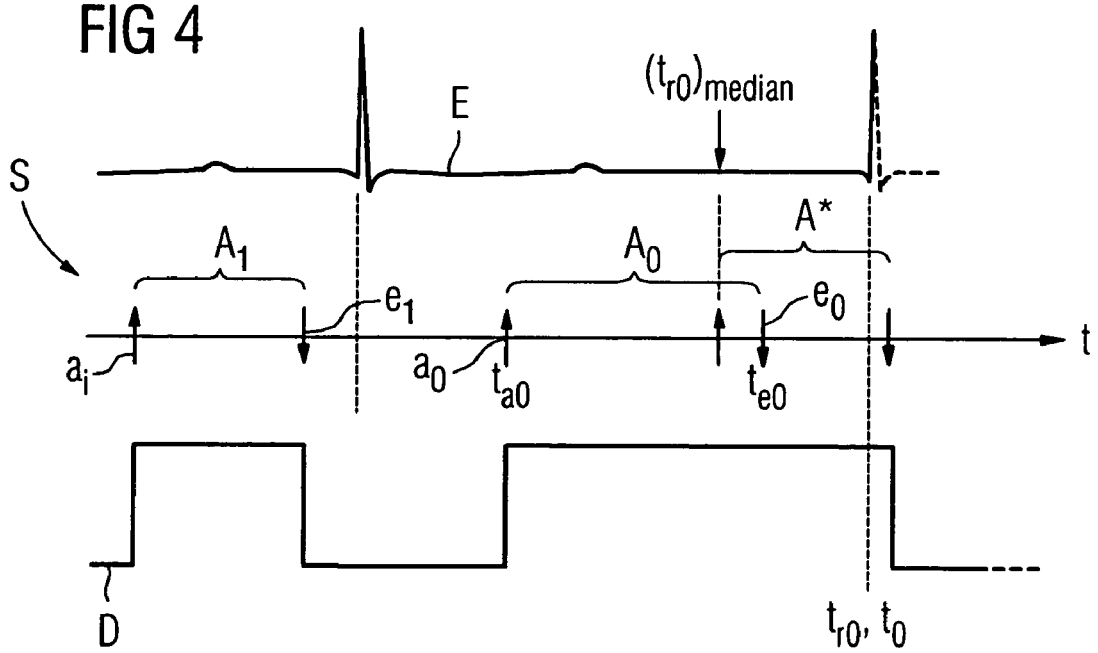

MEDICAL IMAGING METHOD AND AN ASSOCIATED APPARATUS

PRIORITY STATEMENT

The present application hereby claims priority under 35 U.S.C. §119 on German patent application number DE 10 2005 036 963.4 filed Aug. 5, 2005, the entire contents of which is hereby incorporated herein by reference.

FIELD

The invention generally relates to a medical imaging method. For example, it may relate to a method for creating an image data record of the heart and/or blood vessels of a patient, in particular to a so-called rotation angiography method or a so-called cardio scan in the course of computed tomography imaging. The invention further generally relates to an apparatus, such as one for carrying out the method for example.

BACKGROUND

There is the general problem in medical imaging methods for imaging the heart and the blood vessels, in particular the pericardiac ones, that because of the heart beats the body region to be recorded is subject to a continuous periodic movement on the basis of which it is possible to compare directly with one another only images that have been recorded at the same point in the cardiac cycle. This circumstance is problematic, particularly in the case of X-ray tomography recording methods in the case of which the image data record (tomogram) to be created is calculated by backprojection of a multiplicity of projection images recorded from a different projection angle. The backprojection manages to be free from interference only when the basic projection images image an identical three-dimensional body region. However, if because of the movement of the heart, for example, the body region moves during the recording of the projection images, this is reflected in movement artifacts in the resulting tomogram, and these can substantially limit the quality of the latter.

It is therefore customary in the case of X-ray tomographic pictures of the heart and/or the pericardiac blood vessels to synchronize the recording of the projection images with the cardiac rhythm of the patient in such a way that the imaging is respectively performed in the rest phase of the cardiac cycle. An appropriate triggering of the imaging is performed in this case with the aid of the ECG (electrocardiogram) signal from the patient. The ECG-assisted control of imaging is also denoted as "ECG gating". The ECG assisted modulation of the tube current is denoted here as ECG pulsing.

The more so as only the projection images recorded within the rest phases of the cardiac movement can be used to reconstruct the tomogram, it is also only during the time windows corresponding to these rest phases that there is a need to apply X-radiation to the patient. In order to reduce the X-ray dose applied to the patient, it would be desirable, on the other hand to reduce the irradiation as far as possible outside these time windows.

In conventional imaging methods with ECG pulsing, the normal approach is to estimate the time window following in time, that is to say occurring in the direct future, by forming the mean or the median over a prescribed number of preceding cardiac cycles, and to generate a recording pulse, corresponding to the precalculated time window, for modulating the tube current during imaging.

In the event of irregularities in the cardiac rhythm, that is to say a change in the heart rate on the time scale of one or a few cardiac cycles, this method always leads, however, to a more or less pronounced miscalculation of the predicted time window.

In order to ensure that the image information required for image reconstruction is obtained despite the uncertainty in the calculation of the recording pulses, in the case of conventional recording methods the radiation is not completely switched off outside the predicted time windows, but reduced to a specific fraction, for example 25%. It is thereby possible to calculate a tomogram even in the event of a miscalculation of the time window. However, as a rule a miscalculation of the time window is reflected in a substantially restricted quality of the tomogram, in particular in increased image noise.

Because of these restrictions, in clinical practice ECG pulsing is normally used only with patients who have a very uniform cardiac rhythm. In many instances, by contrast, ECG pulsing is switched off during imaging, and so the patient experiences a full dose of irradiation during the entire scan, and a substantially greater dose than required is therefore applied.

SUMMARY

A medical imaging method for generating an image data record is disclosed, in at least one embodiment of the invention, that is particularly suitable for imaging the heart and/or the blood vessels of a patient. At least one embodiment of the invention further specifies an apparatus that is particularly suitable for carrying out the method.

With reference to the method of at least one embodiment, from an ECG signal of a patient to be examined, a series, tuned to the cardiac cycle of the patient, of recorded pulses is derived by which the imaging can be driven in a pulsed fashion. The method provides for determining an initial instant and a final instant of a future recording pulse taking account of at least one parameter that characterizes an irregularity of the cardiac rhythm. Such parameters are denoted below as variability parameters. An irregularity of the cardiac rhythm is any temporal change in the heart rate or cardiac cycle duration on the timescale of a cardiac cycle or a few cardiac cycles. In particular, the recording pulses are selected here in such a way that they are temporarily tuned to the rest phase of the heart inside the cardiac cycle.

Taking account of one or more variability parameters when calculating the recording pulses improves the robustness of the ECG pulsing substantially, and so it is now also possible to use ECG pulsing in many instances where imaging previously had to be performed with the patient under a high dose of continuous irradiation because of an excessively irregular cardiac rhythm. Consequently, on average a substantial reduction in the radiation burden per recorded image is achieved for the patient. However, even in those cases in which the use of ECG pulsing was already previously possible, the inventive method generally achieves a marked improvement by virtue of the fact that the irradiation dose is further reduced as a result of an improved temporal fitting of the recording pulses to the data segments actually required for imaging.

At least one variability parameter is preferably determined statistically by analyzing a prescribed number of preceding cardiac cycles. Here, the minimum duration, the maximum duration of the analyzed cardiac cycles or the standard deviation of the cardiac cycle duration are taken into account on their own or in combination as variability parameter. In addition or as an alternative, a trend of the cardiac cycle duration over the analyzed cardiac cycles and, if appropriate, the standard deviation of the trend determined are taken into account as variability parameter. Denoted as trend here is a function, determined by (in particular linear) regression, of the cardiac cycle duration that characterizes an averaged change in the cardiac cycle duration during the analyzed preceding cardiac cycles, and enables the future cardiac cycle duration to be determined by extrapolation.

In addition or as an alternative to one of the several statistical variability parameters previously described, it is preferred also to take account of an extraordinary variation in the cycle duration, that is to say an extraordinarily long and/or short duration of the current cardiac cycle, when determining the recording pulses.

The duration of a cardiac cycle is generally determined by measuring the temporal spacing between two consecutive R deflections (or R waves) of the ECG signal. An extraordinarily long or short cycle duration is correspondingly detected when the R deflection terminating the current cardiac cycle is detected in a significantly delayed or premature fashion with respect to a statistically determined estimated instant.

In the case of a delayed R deflection, it is expedient to initiate an additional recording pulse when the predicted R deflection had not yet been detected up to the estimated instant such that the lengthened cardiac cycle is utilized optimally for imaging. In the case of a premature R deflection (denoted below as extra systole), it is expedient to start a new recording pulse as soon as the premature R deflection is detected. This measure is advantageous in order to be able to determine an optimal time window for imaging with a comparatively high reliability even in the case of an extra systole, and thus of a severe irregularity of the cardiac cycle.

The imaging method of at least one embodiment includes, for example, an imaging method based on X-radiation, in particular an X-ray tomography method. Here, the imaging is driven in accordance with the recording pulses in such a way that the X-radiation applied to the patient is increased during the recording pulses to a comparatively high uptake of the X-ray dose, while outside the recording pulses the X-radiation is reduced to a comparatively slight basic amount of the X-ray dose, in particular to approximately 25% of the uptake value. Furthermore, however, the inventive ECG pulsing principle can also be used advantageously in the context of other medical imaging methods in which it is required or expedient to synchronize the imaging with the heart rate.

An apparatus of at least one embodiment of the invention comprises an imaging unit for creating an image data record of the heart and/or the blood vessels of a patient, and also an ECG unit for acquiring an ECG signal of the cardiac rhythm of the patient. The apparatus further comprises a control unit that is designed to trigger the imaging unit in accordance with at least one embodiment of the method previously described; that is to say to drive it in a pulsed fashion tuned to the cardiac rhythm of the patient. The imaging unit may be, for example, an X-ray tomograph in the wider sense, in particular a computed tomograph or a rotation angiograph.

BRIEF DESCRIPTION OF THE DRAWINGS

An example embodiment of the invention is explained in more detail below with the aid of the drawings, in which:

FIGS. 3 and 4 show in illustration in accordance with FIG. 2 the ECG signal, the control signal and the X-ray dose in the case of a delayed R deflection of the ECG signal.

Mutually corresponding parts and variables are always provided with the same reference symbols in all the figures.

DETAILED DESCRIPTION OF THE EXAMPLE EMBODIMENTS

Figure 1:
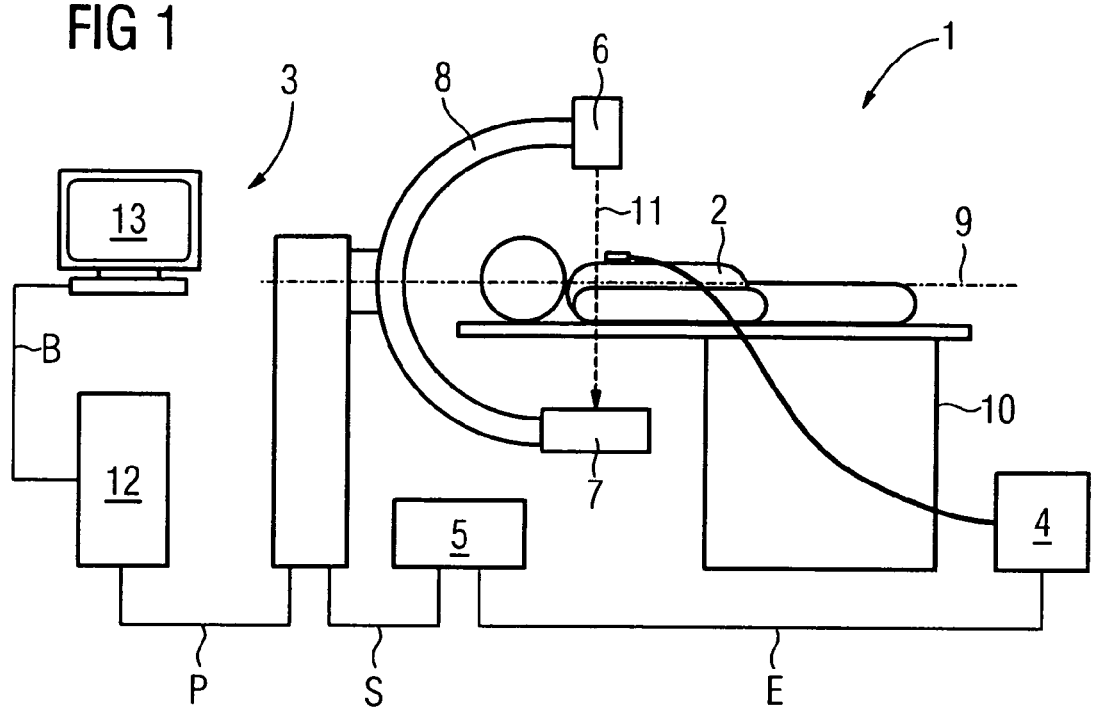
FIG. 1 shows a schematic of an X-ray tomography apparatus for generating an image data record of the heart and/or the blood vessels of a patient, having an imaging unit, an ECG unit and a control unit for driving the imaging unit.

FIG. 1 shows an X-ray tomography apparatus 1 for generating an in particular three dimensional image data record B (or tomogram) of the heart or the blood vessels of a patient 2.

The apparatus 1 essentially includes an imaging unit 3, an ECG unit 4 and a control unit 5.

The imaging unit 3 includes an X-ray machine 6 and an X-ray detector 7 that are fastened opposite one another on a C arc 8 (or a gantry). The C arc 8 is rotatably mounted in this case in such a way that the X-ray machine 6 and the X-ray detector 7 are rotated about a common isocentric axis 9 by rotating the C arc 8.

In order to support the patient 2, the apparatus 1 further includes a patient table 10 on which the patient 2 is supported in such a way that a body region of the patient 2 that is to be examined—thus, in particular, the heart or the blood vessels to be examined—is positioned between the X-ray machine 6 and the X-ray detector 7, and thus, in particular, in the beam path 11 of the X-radiation emitted by the X-ray machine 6 in the direction of the X-ray detector 7.

In the course of the imaging, the imaging unit 3 records a multiplicity of X-ray projection images P from a different projection direction in conjunction with rotation of the C arc 8. The X-ray projection images P are fed to a valuation unit 12 that calculates the image data record B from the X-ray projection images D, for example by way of numerical back-projection. In order to display the image data record B, the imaging unit 3 further includes input and output devices, for example a display screen 13.

In order to prevent the image data record B from being falsified by movement artifacts, to be ascribed to cardiac movement, during the reconstruction from the projection images P, the imaging unit 3 is driven by the control unit 5 in such a way that the projection images P are recorded during specific mutually corresponding phases of the cardiac movement, in particular during the rest phases of the cardiac movement. The control unit 5 determines these phases with the aid of an ECG signal E of the cardiac rhythm of the patient 2, which is acquired by the ECG unit 4 and fed to the control unit 5 as input variable.

The control unit 5, in turn, generates a control signal S that is fed to the imaging unit 3 in order to drive the X-ray machine 6 and the X-ray detector 7.

Figure 2:
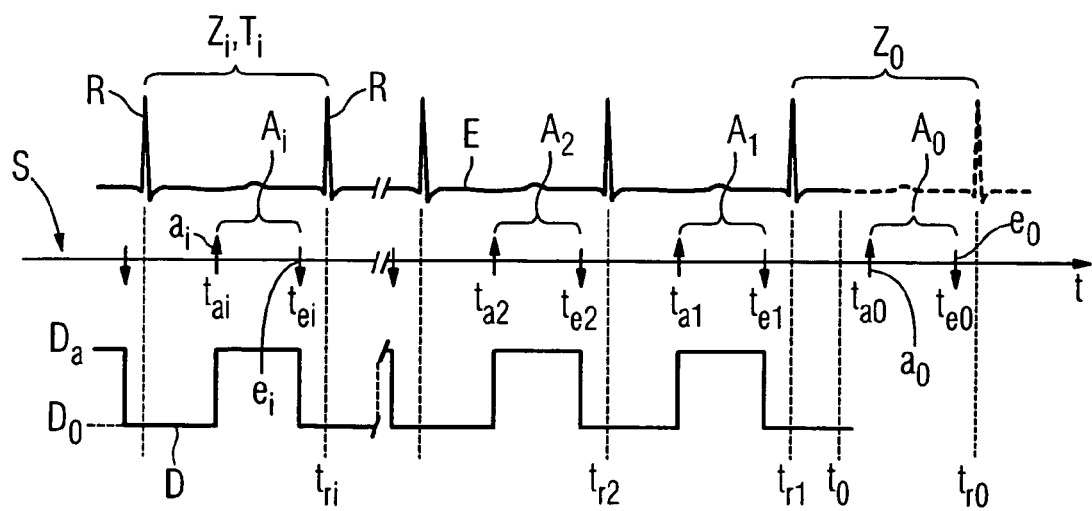
FIG. 2 shows in a schematic diagram plotted against time, an ECG signal acquired by the ECG unit, a control signal, output by the control unit to the imaging unit and comprising a series of recorded pulses derived from the ECG signal, and the X-ray dose, set in accordance with the recording pulses, of the imaging unit.

As is indicated schematically in FIG. 2 in the diagram plotted against time t, the control signal S includes a series of recording pulses $A_i$ (i=0, 1, 2, . . . ) each of which is temporally bounded by an initial signal $a_i$ and a final signal $e_i$ (in each case i=0, 1, 2, . . . ). The initial signal $a_i$ therefore marks an initial instant $t_{ai}$ (i=0, 1, 2, . . . ), and the final signal $e_i$ marks a final instant $t_{ei}$ (i=0, 1, 2, . . . ) of the associated recording pulse $A_i$. Here, the recording pulses $A_i$ are given, for example, by a rectangular pulse of the control signal S in each case, the associated initial signal $a_i$ being given by a rising edge, and the final signal $e_i$ being given by a forwarding edge of the control signal S.

In the illustration, recording pulses $A_i$ already output (that is to say previous ones) are assigned a positive running index, that is to say i>0, the value of the running index i increasing with increasing temporal spacing of the recording pulse $A_i$ with respect to the current instant $t_0$. By contrast, the recording pulse following in the immediate future with respect to the current instant $t_0$ is assigned the running index i=0, that is to say denoted as recording pulse $A_0$. A corresponding indexing is used to distinguish the initial and final signals $a_i$, $e_i$ respectively, and the associated instants $t_{ai}$, $t_{ei}$ respectively.

As is to be seen from FIG. 2 with the aid of the contrasting of the control signal S with the ECG signal E, the recording pulses $A_i$ are tuned to the cardiac rhythm of the patient 2 in such a way that a recording pulse $A_i$ normally occupies a prescribed section of a cardiac cycle $Z_i$ (i=0, 1, 2, ...), in particular the time interval stretching over between 40% and 70% of the cardiac cycle duration $T_i$ (i=0, 1, 2, ...). Each cardiac cycle $Z_i$ is bounded in this case by the respective instant $t_{ri}$ (i=0, 1, 2, ...) of two consecutive R deflections R (or R waves) of the ECG signal E.

In accordance with the control signal S the X-ray dose D of the X-radiation emitted by the X-ray machine 6 is controlled in turn in such a way that the X-ray dose D is set for the duration of each recording pulse $A_i$ to a comparatively high recorded value $D_a$, while the X-ray dose D is reduced outside the recording pulse $A_i$ to a low basic value $D_0$ that is approximately 25% of the recorded value $D_a$.

In order to output the initial signal $a_0$ and the final signal $e_0$ of the future recording pulse $A_0$, the control unit 5 calculates the associated initial and final instant $t_{a0}$, $t_{e0}$, respectively, the control unit 5 estimating the expected cardiac cycle duration, required for this reason, of the current cardiac cycle $Z_0$ by statistical analysis of the last n (n=2, 3, 4, ...), in particular n=3, preceding cardiac cycles $Z_1, Z_2, ..., Z_n$ using the method described in more detail below.

For the later calculation of the instants $t_{a0}$ and $t_{e0}$, the control unit 5 firstly carries out three estimates for the instant $t_{r0}$ of the next R deflection R of the ECG signal E.

a) Maximum Duration $T_{max}$ of the Cardiac Cycle $Z_0$

In the first step, the linear trend of the last n cardiac cycles $Z_1, Z_2, ..., Z_n$ is determined with the aid of a linear regression. With the aid of the vectors X=[−n, −n+1, ..., −1] and Y=[$T_n$, $T_{n-1}, ..., T_1$], the auxiliary variables become $$S_X = \sum_{i=1}^{n} X_i;$$

$$S_Y = \sum_{i=1}^{n} Y_i;$$

$$S_{XX} = \sum_{i=1}^{n} X_i^2;$$

$$S_{YX} = \sum_{i=1}^{n} X_i Y_i;$$

$$\Delta = n \cdot S_{XX} - (S_X)^2$$

equ. 1

A trend line with gradient a and axial intersect b $$a = \frac{1}{\Delta} \cdot (n S_{XY} - S_X S_Y);$$

$$b = \frac{1}{\Delta} \cdot (S_{XX} S_Y - S_X S_{XY}).$$

equ. 2 is therefore yielded as a linear function with least error square.

Moreover, the standard deviation of the actual cardiac cycle duration $T_i$ of the trend line is determined by $$\sigma = \frac{\sqrt{\frac{1}{n} \cdot \sum_{i=1}^{n}(T_i + a \cdot i - b)^2}}{\frac{1}{n} \cdot \sum_{i=1}^{n}(a \cdot i - b)}$$

equ. 3

The estimated, maximum duration $T_{max}$ of the cardiac cycle $Z_0$ is determined as the maximum of the last n cardiac cycles $Z_{1,2}, ..., Z_n$ and of the cardiac cycle duration increased by an amount $\lambda_T$ and estimated by the trend, the standard deviation $\sigma$ additionally being taken into account $$T_{max} = (1+\lambda_V \sigma) \cdot \max\{\max\{T_i | i=1,2,...,n\}, (1+\lambda_T) \cdot b\}$$

equ. 4

The parameters $\lambda_V$ and $\lambda_T$ are selected empirically such that a workable compromise is found between the mutually contradictory aspects of a maximum dose saving (and correspondingly small values for $\lambda_V$ and $\lambda_T$) and adequate reliability in the dimensioning. $\lambda_V$ is preferably thus selected in the limits of 0 to 5, in particular as $\lambda_V$=2, 4. $\lambda_T$ is preferably selected in the limits of 0 to 0.2, in particular as $\lambda_T$=0.1.

The next R deflection R is therefore to be expected at the instant $$(t_{r0})_{max} = t_{r1} + T_{max}$$

equ. 5 at the latest.

b) Minimum Duration $T_{min}$ of the Cardiac Cycle $Z_0$

The minimum duration $$T_{min} = \max\{(1-\lambda_V \sigma) \cdot \min\{\min\{T_i | i=1,2,...,n\}, (1-\lambda_T) \cdot b\}, T_{theo.min}\}$$

equ. 6 is calculated analogously with the aid of the auxiliary variables determined according to equ. 1, this variable in accordance with equ. 6 being limited for reasons of plausibility to a physiologically sensible minimum duration $T_{theo.min}$ (for example 100 ms).

Consequently, the next R deflection R is to be expected at the instant $$(t_{r0})_{min} = t_{r1} + T_{min}$$

equ. 7 at the earliest.

c) Most Likely Duration of the Cardiac Cycle $Z_0$

The most likely instant for the occurrence of the next R deflection R is calculated in the present exemplary embodiment by way of $$(t_{r0})_{median} = t_{r1} + T_{median}$$

equ. 8

$T_{median}$ is estimated by way of $$T_{median} = \text{median}\{T_i | i=1,2,...,n\}$$

equ. 9

As an alternative to this, the most likely cardiac cycle duration can also be determined by forming the mean over the cardiac cycle duration $T_i$ of the preceding cardiac cycles Z.

The initial and final instant $t_{a0}$ and $t_{e0}$, respectively, of the recording pulse $A_0$ to be calculated in advance is now determined using $$t_{a0} = t_{r1} + p_{Start} \cdot T_{min} \qquad \text{equ. 10a}$$

or $$t_{e0} = t_{r1} + p_{Ende} \cdot T_{max} + T_{recon} \qquad \text{equ. 10b}$$

$p_{Start}$ and $p_{Ende}$ define the window, normally allocated to the recording pulses $A_i$, inside the cardiac cycle $Z_i$ (for example $p_{Start}=0.4$ and $p_{Ende}=0.7$), and $$T_{recon} = \frac{T_{rot}}{2\pi} \cdot \left(\pi + 2 \cdot a\sin\left(\frac{R_m}{2R_f}\right) + \alpha_{Trans}\right) \qquad \text{equ. 11}$$

represent the time for the data interval in the case of a so-called reconstruction by partial rotation (or quick scan reconstruction). Here, $T_{rot}$ denotes the time for a complete rotation of the X-ray machine 6 and of the X-ray detector 7 by 360°, $R_m$ (for example 250 mm) denotes the typical dimension of a cardio measuring field, $R_f$ denotes the focal track radius (for example 570 mm), and $\alpha_{trans}=\pi/12$ denotes the transition of the sinogram weighting used in the reconstruction.

Information relating to the irregularity of the cardiac rhythm during the analyzed cardiac cycles $Z_1, Z_2, \ldots, Z_n$ during the calculation of the time window $A_0$ is utilized by taking account of the variables $T_{max}, T_{min}, a, b,$ and $\sigma$. The variables $T_{max}, T_{min}, a, b$ and $\sigma$ in this case represent "variability parameters" in the sense of the present definition.

In a departure from the calculation of the recording pulses $A_i$ using equ. 10a and 10b, the control signal S is modified when an R deflection R of the ECG signal E occurs in an extraordinarily delayed or premature fashion.

I) Delayed R Deflection: $t_{r0} > (t_{r0})_{median}$

An R deflection R of the ECG signal E is judged to be delayed when the R deflection has not yet actually been detected at the most likely instant $(t_{r0})_{median}$ using equ. 8, for example.

If the recording pulse $A_0$ is already terminated at this instant, an additional recording pulse A* is—as illustrated in FIG. 3—initiated at the instant $(t_{r0})_{median}$. If, by contrast, the recording pulse $A_0$ has not yet terminated at the instant $(t_{r0})_{median}$, the previous recording pulse $A_0$ is overwritten with the additional recording pulse A*, that is to say the final signal $e_0$ originally provided at the instant $t_{e0}$ is ignored (FIG. 4).

The additional recording pulse A* is truncated in accordance with the following rule described under point III).

II) Premature R Deflection: $t_{r1} < t_{r2} + (1-\lambda_X) \cdot T_{median}$

An extraordinary premature R deflection (or an extra systole R*) exists by definition when an R deflection of the ECG signal E has occurred at a prescribed fraction $\lambda_X$ of the most likely cardiac cycle duration $T_{median}$ before the predicted instant $(t_{r1})_{median}$. The parameter $\lambda_X$ has, for example, the value 0.2. that is to say, an R deflection R is detected as extra systole R* in the event of more than 20% shortening of the cardiac cycle duration with respect to the most likely cardiac cycle duration $T_{median}$.

Figure 5:
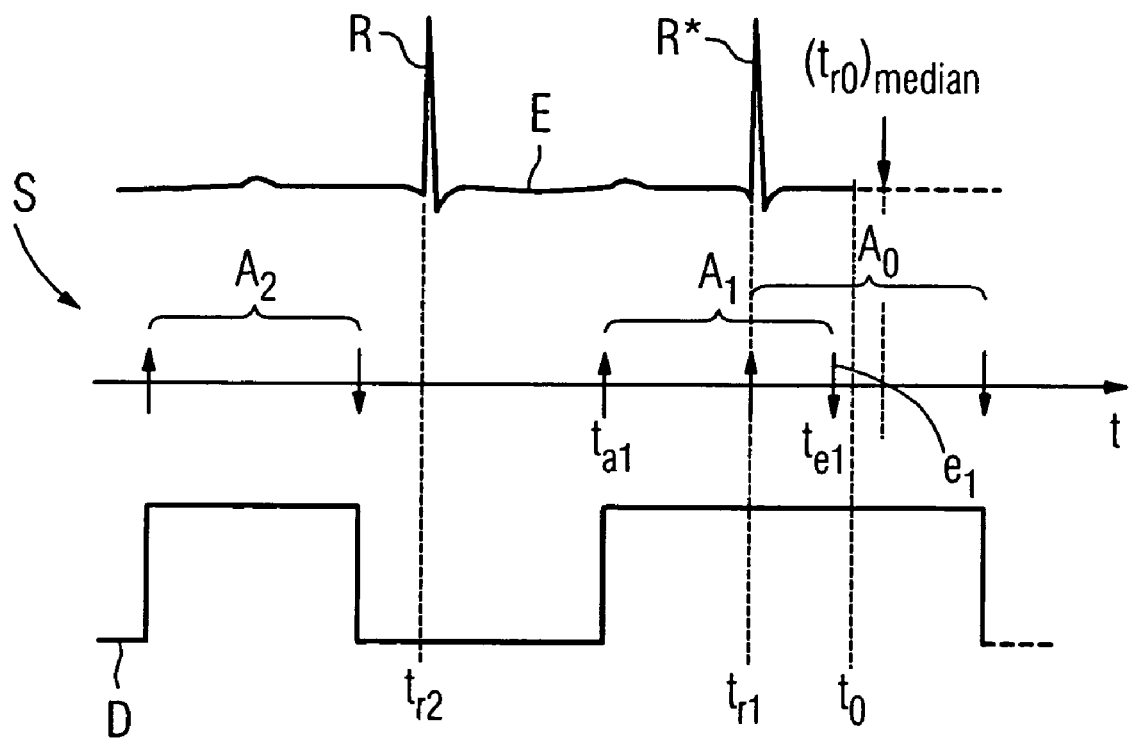
FIG. 5 shows, in illustration in accordance with FIG. 2, the ECG signal, the control signal and the X-ray dose in the case of an extra systole, that is to say a premature R deflection of the ECG signal.

In this case, a new recording pulse $A_0$ is initiated directly upon the occurrence of the extra systole R* (FIG. 5).

Given a temporal overlap of the recording pulse $A_0$ and $A_1$, the final signal $e_1$ provided for the first recording pulse $A_1$ at the instant $t_{e1}$ is again ignored (point IV)). The final instant $t_{e0}$ of the new recording pulse $A_0$ is likewise defined in this case by the rule described below in relation to point III).

III) R Deflection During the Recording Pulse: $t_{r0} < t_{e0}$

If an R deflection R or R* occurs during a recording pulse $A_0$, an optimized duration of this recording pulse $A_0$ is calculated retrospectively. The final instant $(t_{e0})_{opt}$, optimized in accordance with this calculation, of the recording pulse $A_0$ is given in this case by $$(t_{e0})_{opt} = t_{r1} + p_{Ende} \cdot (t_{r1} - t_{r0}) + T_{recon} \qquad \text{equ. 12}$$

The recording pulse $A_0$ is terminated in this case at the instant $$t_{e0} = \max\{(t_{e0})_{opt}, t_{r0}\} \qquad \text{equ. 13}$$

If an additional recording pulse A* is inserted in the case of a delayed R deflection R (point I), equ. 13 defines the final instant of the additional recording pulse A*.

IV) Overlapping Recording Pulses: $t_{e(i+1)} > t_{ai}$

If a recording pulse $A_i$, A* is initiated before the preceding recording pulse $A_{i+1}$ is terminated, the newer recording pulse $A_i$, A* generally overshoots the previous recording pulse $A_{i+1}$. In particular, in this case the final instant $t_{e(i+1)}$ intended for the previous recording pulse $A_{i+1}$ is ignored.

The information relating to the occurrence of an R deflection R is delayed by a prescribed time period on the basis of diverse latencies of the system components (signal transmission, detection of the R deflections, etc.). The instants used for the calculation are always to be understood here as data in real time, that is to say as having been corrected for the latencies, if the calculated events take place later than at the current time.

The above described method improves the robustness of the ECG pulsing considerably, that is to say the "lost high current intervals", which are not used for imaging with a high dose because of a misestimation of the required data segments, for example during the calculation of the rest phases of the cardiac rhythm, are substantially reduced in number and length by comparison with conventional pulsing methods. It is possible by using the above described method to achieve a quasi ideal correspondence (wasted segments<5% of the rotation time) for 86% of all patients examined, while the corresponding quota is approximately 13% for a conventional pulsing method.

Further, elements and/or features of different example embodiments may be combined with each other and/or substituted for each other within the scope of this disclosure and appended claims.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An imaging method for creating an image data record of at least one of a heart and blood vessels of a patient, comprising:

deriving, from an ECG signal of a cardiac rhythm of the patient, acquired from an ECG unit a series, tuned to the cardiac rhythm, of recording pulses by which imaging is driven in a pulsed fashion, an initial instant and a final instant of a next recording pulse being determined by taking account of variability parameters characterizing an irregularity of the cardiac rhythm; and creating the image data record based the variability parameters, wherein
the variability parameters include,
a linear trend line of a cycle duration of the analyzed cardiac cycles, where the linear trend line is determined statistically using a linear regression function that analyzes a prescribed number of preceding cardiac cycles,
a standard deviation of the cycle duration based on the linear trend line,
a maximum duration based on the standard deviation and a maximum of cycle durations of the prescribed number of preceding cardiac cycles and a first estimated cycle duration determined according to the linear trend line and increased based on a limiting value, and
a minimum duration based on the standard deviation and a minimum of the cycle durations of the prescribed number of preceding cardiac cycles and a second estimated cycle duration determined according to the linear trend line and decreased based on the limiting value.

2. The imaging method as claimed in claim 1, wherein the initial instant of the next recording pulse is determined by taking account of the minimum duration of the analyzed cardiac cycles, and the final instant of the next recording pulse is determined by taking account of the maximum duration of the analyzed cardiac cycles.

3. The imaging method as claimed in claim 2, wherein a scanner deviation of a cycle duration with reference to an least one of a mean and median of the analyzed cardiac cycles is taken into account for at least one of the variability parameters.

4. The imaging method as claimed in claim 1, wherein a scanner deviation of a cycle duration with reference to an least one of a mean and median of the analyzed cardiac cycles is taken into account for at least one of the variability parameters.

5. The imaging method as claimed in claim 1, wherein,
an estimated instant of the next R deflection of the ECG signal is determined by forming at least one of a mean and median over a prescribed number of preceding cardiac cycles, and wherein
an additional recording pulse is initiated when the predicted R deflection does not occur up to this estimated instant.

6. The imaging method as claimed in claim 5, wherein a scanner deviation of a cycle duration with reference to an least one of a mean and median of the analyzed cardiac cycles is taken into account for at least one of the variability parameters.

7. The imaging method as claimed in claim 1, wherein,
an estimated instant of the next R deflection of the ECG signal is determined by forming at least one of a mean and median over a prescribed number of preceding cardiac cycles, and wherein
a new recording pulse is immediately initiated whenever the next R deflection occurs prematurely by more than a prescribed tolerance time with respect to the estimated instant.

8. The imaging method as claimed in claim 1, wherein the imaging is performed by applying X-radiation to the patient, an X-ray dose of the X-radiation applied to the patient being switched to a comparatively high recording value during each recording pulse, and to a comparatively low basic value between two consecutive recording pulses.

9. The imaging method as claimed in claim 8, wherein the basic value corresponds to approximately 25% of the recording value.

10. The imaging method as claimed in claim 1, wherein the imaging is performed using X-ray tomography by recording a plurality of X-ray projection images, from which the image data record is created by backprojection, at a varying projection angle.

11. An imaging unit configured to create an image data record of at least one of a heart and blood vessels of a patient, the imaging unit comprising:
an ECG unit configured to acquire an ECG signal of a cardiac rhythm of the patient; and
a control unit configured to derive a series of recording pulses, tuned to the cardiac rhythm, from the ECG signal, and to drive the imaging unit in a pulsed fashion in accordance with the recording pulse, an initial instant and a final instant of a next recording pulse being determined by taking account of variability parameters characterizing an irregularity of the cardiac rhythm, wherein
the variability parameters include,
a linear trend line of a cycle duration of the analyzed cardiac cycles, where the linear trend line is determined statistically using a linear regression function that characterizes an averaged change from cycle to cycle in the cycle duration during a prescribed number of preceding cardiac cycles,
a standard deviation of the cycle duration based on the linear trend line,
a maximum duration based on the standard deviation and a maximum of cycle durations of the prescribed number of preceding cardiac cycles and a first estimated cycle duration determined according to the linear trend line and increased based on a limiting value, and
a minimum duration based on the standard deviation and a minimum of the cycle durations of the prescribed number of preceding cardiac cycles and a second estimated cycle duration determined according to the linear trend line and decreased based on the limiting value.

12. The imaging unit as claimed in claim 11, further comprising:
an X-ray machine/detector unit, rotatable about an isocentric axis, configured to record X-ray projection images; and
an evaluation unit configured to create the image data record by numerical backprojection from a plurality of X-ray projection images recorded at a different projection angle.

13. An imaging unit configured for creating an image data record of at least one of a heart and blood vessels of a patient, comprising:
means for acquiring an ECG signal of a cardiac rhythm of the patient; and
means for deriving a series of recording pulses, tuned to the cardiac rhythm, from the ECG signal, and for driving the imaging unit in a pulsed fashion in accordance with the recording pulse, an initial instant and a final instant of a next recording pulse being determined by taking account of variability parameters characterizing an irregularity of the cardiac rhythm, wherein
the variability parameters include,
a linear trend line of a cycle duration of the analyzed cardiac cycles, where the linear trend line is determined statistically using a linear regression function that characterizes an averaged change from cycle to cycle in the cycle duration during a prescribed number of preceding cardiac cycles,
a standard deviation of the cycle duration based on the linear trend line,
a maximum duration based on the standard deviation and a maximum of cycle durations of the prescribed number of preceding cardiac cycles and a first estimated cycle duration determined according to the linear trend line and increased based on a limiting value, and
a minimum duration based on the standard deviation and a minimum of the cycle durations of the prescribed number of preceding cardiac cycles and a second estimated cycle duration determined according to the linear trend line and decreased based on the limiting value.

14. The imaging unit as claimed in claim 13, further comprising:
means, rotatable about an isocentric axis, for recording X-ray projection images; and
means for creating the image data record by numerical backprojection from a plurality of X-ray projection images recorded at a different projection angle.

* * * * *